United States Patent [19]
Gattoni-Celli et al.

[11] Patent Number: 6,063,375
[45] Date of Patent: May 16, 2000

[54] SEMIALLOGENEIC CELL HYBRIDS AND RELATED METHODS FOR TREATING CANCER

[75] Inventors: Sebastiano Gattoni-Celli, Mt. Pleasant; Danforth A. Newton, III, Beaufort; Edward F. McClay, Folly Beach, all of S.C.

[73] Assignee: Medical University of South Carolina, S.C.

[21] Appl. No.: 08/707,920

[22] Filed: Sep. 10, 1996

[51] Int. Cl.[7] ............................. A61K 48/00; C12N 15/85
[52] U.S. Cl. ......................... 424/93.21; 435/325; 435/346
[58] Field of Search .................................. 435/346, 325; 424/93.21

[56] References Cited

FOREIGN PATENT DOCUMENTS

| | | | |
|---|---|---|---|
| 0 197 489 | 4/1986 | European Pat. Off. | ......... C12N 15/00 |
| WO 93/07887 | 4/1993 | WIPO | ............. A61K 37/00 |
| WO 95/16775 | 6/1995 | WIPO | ............. C12N 15/12 |
| WO 95/31208 | 11/1995 | WIPO | ............. A16K 35/14 |

OTHER PUBLICATIONS

Almond et al. "Protection Against SIV in Macaques–Implications for AIDS Vaccine Development" Abstract 209, Biotechnology Against AIDS Conference, Rockville, Maryland, Sep. 25–Oct. 1, 1994.
Kawakami et al., "Indentification of a Human Melanoma Antigen Recognized by Tumor–Infiltrating Lymphocytes Associated with in vivo Tumor Rejection" *Proc. Natl. Acad. Sci. USA*, 91:6458–6462, Jul. 1994.
Kawakami et al., "Cloning of the Gene Coding for a Shared Human Melanonma Antigen Recognized by Autologous T Cells" *Proc. Natl. Acad. Sci. USA*, 91:3515–3519, Apr. 1994.
D'Andrea et al. "Interleukin 10(Il–10) Inhibits Human Lymphocyte Interferon γ–Production by Supressing Natural Killer Cell Stimulatory Factor/IL–12 Synthesis in Accessory Cells", *J. Exp. Med.*, 178:1041–1048, Sep. 1993.
Brichard et al. "The Tyrosinase Gene Codes for an Antigen Recognized by Autologous Cytolytic T Lymphocytes on HLA–A2 Melanomas" *J. Exp. Med.* 178:489–495, Aug. 1993.
Plautz et al. "Immunotherapy of Malignancy by in vivo Gene Transfer into Tumors" *Proc. Natl. Acad. Sci.* 90:4645–4659, May 1993.
Tripp et al. "Interleukin 12 and Tumor Necrosis Factor αare Costimulators of Interferon γ Production by Natural Killer Cells in Severe Combined Immunodeficiency Mice. . . " *Proc. Natl. Acad. Sci. USA* 90:3725–3729, Apr. 1993.
Gastl et al. "Interleukin–10 Production by Human Carcinoma Cell Lines and its Relationship to Interleukin–6 Expression" *Int. J. Cancer* 55:96–101, 1993.
Towensend, Sarah E. and Allison, James P. "tumor Rejection After Direct Costimulation of CD8 T Cells by B7–Transfected Melanoma Cells" *Science* 259:368–370, Jan. 15, 1993.
Chen et al., "Costimulation of Antitumor Immunity by the B7 Countereceptor for the T Lumphocyte Molecules CD28 and CTLA–4" *Cell* 71:1093–1102, Dec. 24, 1992.
Boon, Thierry "Toward A Genetic Analysis of Tumor Rejection Antigens" *Adv. Cancer Res.*, 58: 177–210, 1992.
Stott, E.J. "Anti–Cell Antibody in Macaques" *Nature*, 353:393, Oct. 3, 1991.
Oettgen, Herbert F. and Old, Lloyd J. "The History of Cancer Immunotherapy" in: Biologic Therapy of Cancer, DeVita, VT Jr, Hellman, S, and Rosenberg, SA, Eds., J.B. Lippincott Co., Philadelphia, 1991, pp. 87–119.
Toffaletti et al. "Augmentation of Syngeneic Tumor–Specific Immunity by Semiallogeneic Cell Hybrids" *J. Immunol.* 130(6):2982–2986, Jun. 1983.
Payelle et al. "Adoptive Transfer of Immunity Induced by Semi–Allogeneic Hybrid Cells, Against a Murine Fibrosarcoma" *Int. J. Cancer* 27:783–788, 1981.
Kim et al., "Tumor–Specific Immunity Induced by Somathic Hybrids. I. Lack of Relationship between Immunogenicity and Tumorigenicity of Selected Hybrids" *J. Immunol.* 123(2):733–738, Aug. 1979.
Kim, Byung S. "Tumor–Specific Immunity Induced by Somathic Hybrids. II. Elicitation of Enhanced Immunity Against the Parent Plasmacytoma" *J. Immunol.* 123(2):739–744, Aug. 1979.
Giovanella et al. "Human Neoplastic and Normal Cells in Tissue Culture. I. Cell Lines Derived from Malignant Melanomas and Normal Melanocytes" *J. Natl. Cancer Inst.* 56(6):1131–1142, Jun. 1976.
Parkman, Robertson "Tumor Hybrid Cells: An Immunotherapeutic Agent" *J. Natl. Cancer Inst.* 52(5):1541–1545, May 1974.
Jami, Jacques and Ritz, Evelyne "Expression of Tumor–Specific Antigens in Mouse Somatic Cell Hybrids" *Cancer Res.* 33:2524–2528, Oct. 1973.
Newton et al. "Melanoma Cell Hybrids as Cancer Vaccines" *Proceedings of the Amer. Assoc. for Cancer Res.* vol. 38, p. 398, Abstract 2671, Mar. 1997.
D'Urso et al. "Lack of HLA Class 1 antigen Expression by Cultured Melanoma Cells FO–1 Due to a Defect in $B_2M$ Gene Expression", *J. Clin. Invest.* 87:284–292, Jan. 1991.
Hosoi et al. "A Human–Mouse Hybrid Cell Line Expressing both Human Leukocyte and Histocompatibility–2 Antigens" *Japanese J. of Physiol.* 49:297–304, 1990.

*Primary Examiner*—Bruce R. Campell
*Assistant Examiner*—Anne Marie S. Beckerleg
*Attorney, Agent, or Firm*—Needle & Rosenberg, P.C.

[57] ABSTRACT

An isolated cell having the characteristics of the cell line designated FO-1 #12 is provided. The cell FO-1 #12 is characterized as being $β_2$-microglobulin-deficient, neomycin-resistant and HAT-sensitive. A cell hybrid formed by the fusion of an FO-1 #12 cell or other cell described herein and a mammalian cell is provided. The patient-derived cell can be a tumor cell or other cell, such as a white blood cell. The patient-derived tumor cell can be a melanoma cell, a prostatic carcinoma cell, a colon carcinoma cell, a lung carcinoma cell, a breast carcinoma cell, a pancreatic carcinoma cell, or others. A method of treating AIDS in a patient, comprising administering to the patient a cell hybrid provided herein, wherein the patient-derived white blood cell is derived from the patient being treated, is provided. A method of treating solid tumor in a patient, comprising administering to the patient a cell hybrid as provided herein, wherein the patient-derived tumor cell is derived from the patient being treated, is provided.

17 Claims, 4 Drawing Sheets

SEMIALLOGENEIC CELL HYBRIDS AND RELATED METHODS FOR TREATING CANCER

BACKGROUND OF THE INVENTION

1. Field of the Invention

The invention relates to immunotherapy. More specifically the invention relates to the use of a patient-derived cell/non-patient cell hybrid as a therapeutic vaccine. Most specifically the invention relates to a novel cell line, FO-1 #12, for use in generating a therapeutic vaccine for cancer and Acquired Immunodeficiency Syndrome (AIDS).

2. Background Art

For years cancer has evaded immunotherapeutic treatment. The last few years have registered a dramatic expansion in the understanding of tumor immunology, thanks to a series of major discoveries ranging from the identification and molecular characterization of tumor rejection antigens (1–4), to the discovery of co-stimulating molecules like B7 which are expressed on the surface of antigen-presenting cells and are crucial to the effectiveness of the immune activation associated with presentation of antigenic peptides by major histocompatibility complex (MHC) class I molecules (5,6). However, these discoveries have not led to any significant breakthrough in cancer treatment. Taken together the results of these studies point out a major difficulty in tumor immunotherapy; that antigenicity (i.e., the ability to express a tumor antigen) and immunogenicity (i.e., the ability to induce an effective immune response) are not synonyms. In fact, an increasing body of experimental evidence indicates that tumor antigens are present even in poorly or non-immunogenic tumors. A clearer understanding of these difficulties has led to efforts aimed at greatly amplifying the immunogenicity of tumor cells, by engineering them to express specific molecules (5–7). However, these efforts have met with only limited success, because they are technically complicated and, therefore, of limited use for treating human cancer.

The inability to mount an effective response against spontaneous tumors has also been ascribed to alterations in the immune capacity of the tumor-bearing host. Establishment of immunotolerance in cancer patients may prevent effective immunization (8); in fact, several tumors have been shown to produce IL-10 (9), a cytokine that inhibits the production of a variety of immunoaugmenting cytokines (10,11). This situation further complicates the prospects for immunotherapy.

Jami and Ritz (12) first described the immunization of inbred mice with somatic cell hybrids derived from the fusion of syngeneic tumor cells with allogeneic cells. Specifically, they showed that inbred 129/Sv mice were resistant to the inoculation of a tumorigenic challenge with syngeneic teratocarcinoma cells following pre-immunization with (teratocarcinoma X C3H L-cell) semi-allogeneic somatic cell hybrids. Similar observations were reported by Parkman (13) with tumor cell hybrids obtained by the fusion of EL-4 lymphoma cells (H-$2^b$) with C3H fibroblasts (H-$2^k$). These hybrids specifically immunized C57BL/6 (H-$2^b$) mice against a lethal challenge with EL-4 lymphoma cells. Several subsequent studies also described this immunotherapeutic approach (14–17). These later studies also showed that the adoptive transfer of immunity induced by semiallogeneic cells required T lymphocytes; that the enhanced immunity was not due to an allogeneic effect, but was probably the result of an association of tumor-associated antigens (TAA) with allogeneic molecules; and that the TAA and the alloantigen needed to be on the same cell (the hybrid).

It also has been shown that immunization of experimental primates with allogeneic or xenogeneic (human) lymphocytes protects these animals against a challenge with simian immunodeficiency virus (SIV) grown in allogeneic (simian) or xenogeneic (human) cells (18,19). Since SIV is the simian equivalent of human immunodeficiency virus (HIV), the causative agent of AIDS in humans, these findings have major implications for AIDS vaccine development.

However, in spite of major advances in our understanding of immunology, immunotherapy does not yet represent a routine modality for treatment of cancer or AIDS. Moreover, current immunotherapeutic regimens tend to be cumbersome, labor-intensive, expensive, and only apply to a very limited number of cancer types (mostly melanoma and renal cell carcinoma).

Furthermore, despite the fact that semi-allogeneic tumor cell hybrids were used to immunize experimental animals as long ago as 1973 (12), there have been no successes using semi-allogeneic hybrids to treat human cancer. Similarly, there have been no successes using semi-allogeneic hybrids to treat AIDS. Furthermore, no semi-allogenic tumor cell hybrid exists that can be used to treat human cancer or AIDS.

Thus, this invention provides a novel type of therapeutic vaccine based on patient-specific, irradiated semiallogeneic cell hybrids, that could be used to treat any type of cancer as well as AIDS. The use of the present semiallogeneic cell hybrids is technically straight-forward, and entails modest expense compared to most cancer treatment regimens.

SUMMARY OF THE INVENTION

An isolated cell having the characteristics of the cell line designated FO-1 #12 is provided. An isolated cell or cell line, wherein the cell is deficient in $\beta_2$ microglobulin, resistant to a selectable dominant marker and deficient in a selectable recessive marker is provided. The cell FO-1 #12 is characterized as being $\beta_2$ microglobulin-deficient, neomycin-resistant and HAT-sensitive.

A cell hybrid formed by the fusion of an FO-1 #12 cell or other cell described herein and a mammalian cell is provided. The mammalian cell can be a human patient-derived cell. The patient-derived cell can be a tumor cell or other cell, such as a white blood cell. The patient-derived tumor cell can be a melanoma cell, a prostatic carcinoma cell, a colon carcinoma cell, a lung carcinoma cell, a breast carcinoma cell, a pancreatic carcinoma cell, etc.

A method of making a cell hybrid is provided. The method includes the steps of a) contacting a cell deficient in $\beta_2$ microglobulin, having a selectable dominant marker and having a selectable recessive marker with a patient-derived tumor cell or other cell, under conditions in which cell hybrids are formed; and b) selecting cell hybrids by determining the presence of the dominant marker and the presence of the recessive marker, whereby the presence of both the dominant and recessive markers is correlated with the presence of a cell hybrid. This method can further comprise the step of identifying cells that express HLA class I surface antigens.

A method of treating a solid tumor in a patient, comprising administering to the patient a lethally irradiated cell hybrid, wherein the patient-derived tumor cell is derived from the patient being treated, is provided. Also, a method is provided for treating AIDS in a patient, comprising administering to the patient a lethally irradiated cell hybrid, wherein the patient-derived cell is a white blood cell derived from the patient being treated.

BRIEF DESCRIPTION OF THE DRAWINGS

FIG. 2 shows the surface expression of HLA class I antigens on parental cells (FO-1 #12 and 501) and on tumor cell hybrids (FO-1 #12 ×501) obtained from their fusion. Single-cell suspensions from each culture (indicated at the side of the figure) were subjected to indirect immunofluorescent staining and reacted with second antibody alone (blank), monoclonal antibody (mAb) W6-32 (anti-HLA-A, B,C +$\beta_2$ microglobulin), and mAb PA2.1 (anti-HLA-A2). Fluorescence intensity was determined by flow cytometry on a Becton-Dickinson cell analyzer. Note that FO-1 clone 12 (FO-1) cells do not express HLA class I antigens because they lack 2 microglobulin expression; in contrast, tumor cell hybrids (FO-1 #12 ×501) grown in selective medium containing HAT and the neomycin analog G418 (600 µg/ml) express on the cell surface HLA class I antigens, including HLA-A2 (this antigen derives from 501 parental cells).

DETAILED DESCRIPTION OF THE INVENTION

FO-1 #12 Cell

An isolated cell having the characteristics of the cell line designated FO-1 #12 is provided. An isolated cell or cell line, wherein the cell is deficient in $\beta_2$ microglobulin, resistant to a selectable dominant marker and deficient in a selectable recessive marker is provided.

The cell or cell line as described, wherein the dominant marker is drug or antibiotic resistance is provided. The antibiotic resistance can be to neomycin. There are numerous examples of expression of a selectable dominant marker associated with resistance to drug/antibiotic other than neomycin: hygromycin, methotrexate, α-amanitin, ouabain, etc.

The cell or cell line as described, wherein the recessive marker is sensitivity to aminopterin-containing medium (sensitivity to hypoxanthine +aminopterin +thymidine (HAT)-containing medium) is provided. There are other examples of recessive selectable markers, such as deficiency in thymidine kinase.

The cell FO-1 #12 is characterized as being $\beta_2$ microglobulin deficient, neomycin-resistant and HAT-sensitive. An example of a method for making such a cell is given in the Examples. A cell having the characteristics of the cell line designated FO-1 #12 and deposited on Aug. 27, 1996 with the American Type Culture Collection, 12301 Parklawn Drive, Rockville, Md 20852 under accession number ATCC CRL-12177 is also provided.

Cell Hybrids

A cell hybrid formed by the fusion of an FO-1 #12 cell or other cell described herein and a mammalian cell is provided.

The mammalian cell can be a human patient-derived cell. The patient-derived cell can be a tumor cell or other cell, such as a white blood cell. The patient-derived tumor cell can be a melanoma cell, a prostatic carcinoma cell, a colon carcinoma cell, a lung carcinoma cell, a breast carcinoma cell, a pancreatic carcinoma cell, etc.

A method for making a cell hybrid is provided. The method includes the steps of a) contacting a cell deficient in β2 microglobulin, having a selectable dominant marker and having a selectable recessive marker with a patient-derived tumor cell or white blood cell under conditions in which cell hybrids are formed; and b) selecting cell hybrids by determining the presence of the dominant marker and the presence of the recessive marker, whereby the presence of both the dominant and recessive markers is correlated with the presence of a cell hybrid. This method can further comprise the step of identifying cells that express HLA class I surface antigens. An example of this method is described in detail in the Examples.

The cell hybrid provided herein can be lethally irradiated for use as a therapeutic vaccine for cancer or AIDS. The irradiation step takes place shortly before administration of the hybrid to a patient as further described in the Examples.

Semiallogeneic Cell Hybrids as Therapeutic Vaccines for Cancer and AIDS

A method of treating a solid tumor or AIDS in a patient, comprising administering to the patient a cell hybrid as provided herein, wherein patient-derived tumor cell or white blood cell is derived from the patient being treated, is provided.

The present invention provides a therapeutic vaccine for cancer or AIDS, based on irradiated semiallogeneic cell hybrids, generated by the fusion of patient-derived tumor or white blood cells, respectively, with uniquely modified FO-1 human cells (21). Semiallogeneic cell hybrids can be inactivated by irradiation and injected into the same patient to induce a specific anti-tumor or anti-HIV response, respectively. Since it is much easier and more practical to engineer established cell lines, the present method avoids the many technical problems associated with obtaining sufficient amounts of autologous tumor cells for vaccine preparation. Furthermore, the present hybrids satisfy several important criteria for a successful therapeutic vaccine: 1) Antigens (tumor antigens or AIDS-associated antigens) are derived from the cancer cells or white blood cells of each patient, to achieve maximum specificity; 2) Tumor cell hybrids eliminate the need to establish patient-derived tumor cell cultures, which notoriously constitute a major technical hurdle and may not be representative of the original tumor; 3) FO-1-derived HLA class I antigens may enhance the anti-tumor or anti-HIV response by virtue of the allogeneic presentation of tumor or HIV antigens; 4) Cells exposed to a single lethal dose of ionizing radiation can express HLA class I surface antigens for several days before dying.

The cancer or AIDS treatment method, wherein the cell hybrid is administered in conjunction with a cytokine is also provided. The cytokine can be interleukin-12 (IL-12), granulocyte-macrophage colony-stimulating factor (GM-CSF), interleukin-2 (IL-2), or a combination of these and other adjuvants.

EXAMPLES

Construction of FO-1 #12 Cells

FO-1 human cells are deficient in $\beta_2$ microglobulin production; therefore, they do not express HLA class I surface antigens (22). Expression of a transfected human $\beta_2$ microglobulin gene in FO-1 cells leads to restored expression of HLA class I antigens (23).

Derivation of Hgprt⁻ FO-1 Cells

FO-1 cells were mutagenized by exposing them to a single dose (3 Gy) of γ-radiation (6 Gy/min dose rate) and subsequently plated in complete medium containing the purine analog 6-thioguanine at a concentration of 5 µg/ml. The incorporation into the DNA allows the selection of cells that are deficient for hypoxanthine-guanine phosphoribosyl transferase (hgprt). Several hgprt-deficient (hgprt⁻) FO-1 mutants were isolated and characterized for their sensitivity to hypoxanthine, aminopterin, and thymidine (HAT)-containing medium. A particular hgprt⁻ FO-1 clone with a spontaneous reversion rate to a HAT-resistant (hgprt⁺) phenotype of <1×10⁻⁷ was selected. However, the actual reversion rate must be much lower, since after several months of experimentation, not even a single HAT-resistant FO-1 (hgprt⁺) revertant was found.

Transfection of FO-1 hgprt⁻ Cells

Exponentially growing FO-1 hgprt⁻ cells were transfected, using the calcium phosphate precipitation technique (24), with a plasmid containing the neomycin-resistance gene (25). Neomycin-resistant clones were selected in Dulbecco's modified Eagle's medium (DMEM) with added 10% fetal bovine serum (FBS), 50 units/ml penicillin, 50 $\mu$g/ml streptomycin, and 40 $\mu$g/ml ciprofloxacin (complete medium), containing the neomycin analog geneticin (Gibco) at a concentration of 600 $\mu$g/ml. Neomycin-resistant clones became visible 3 weeks after transfection; and individual clones were expanded for further characterization.

Figure 1:
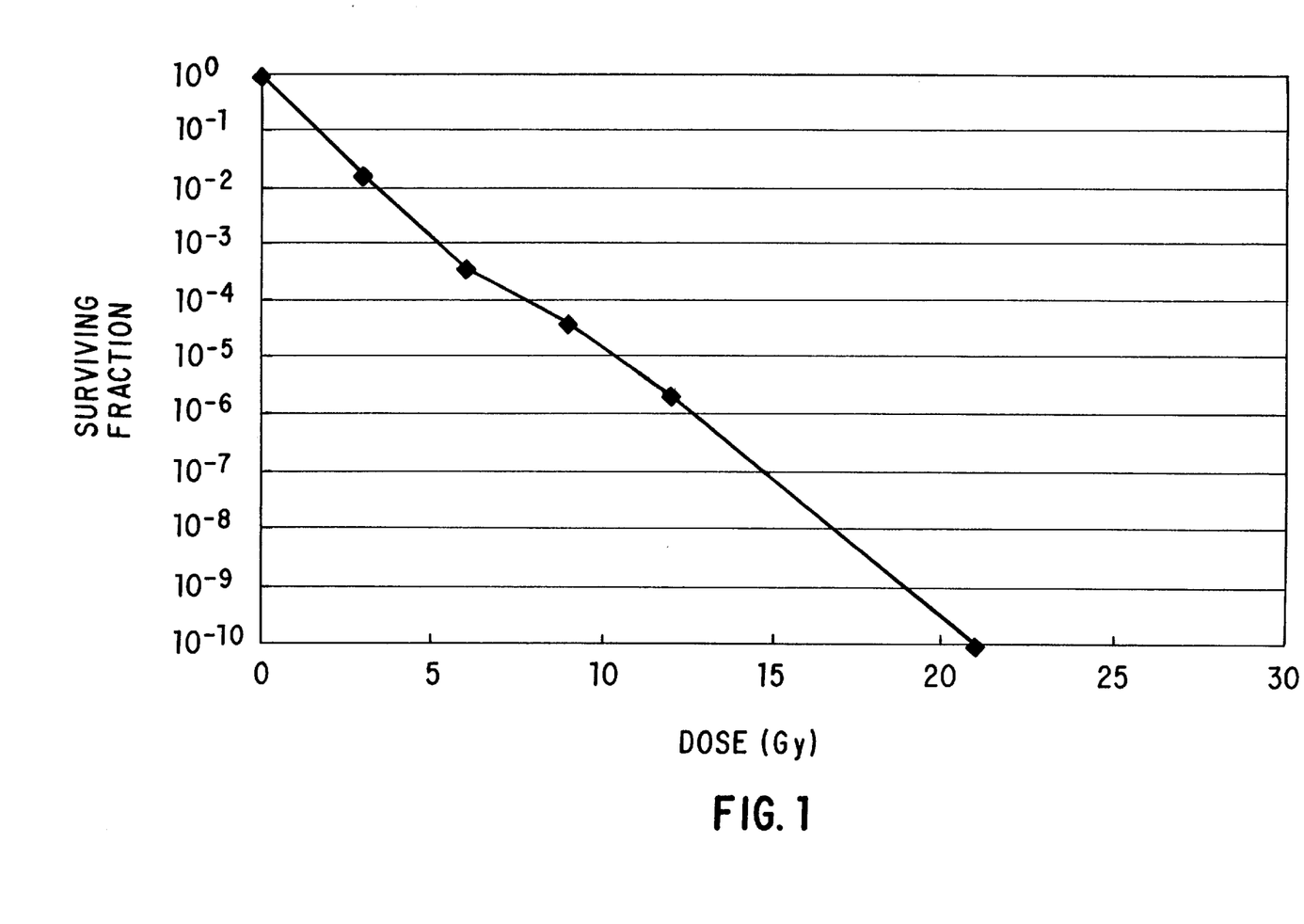
FIG. 1 shows the survival curve of FO-1-neo cells exposed to increasing doses of γ-rays.
Figure 2A:
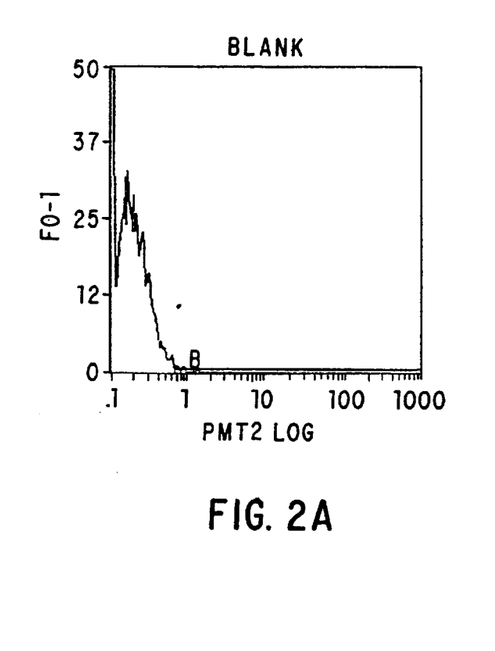
Figure 2B:
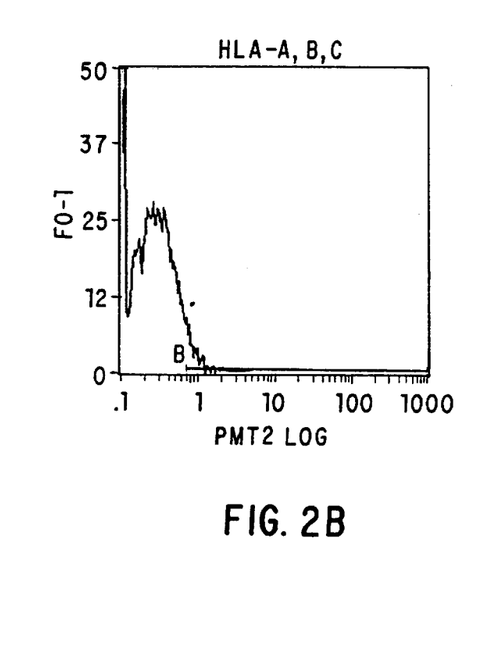
Figure 2C:
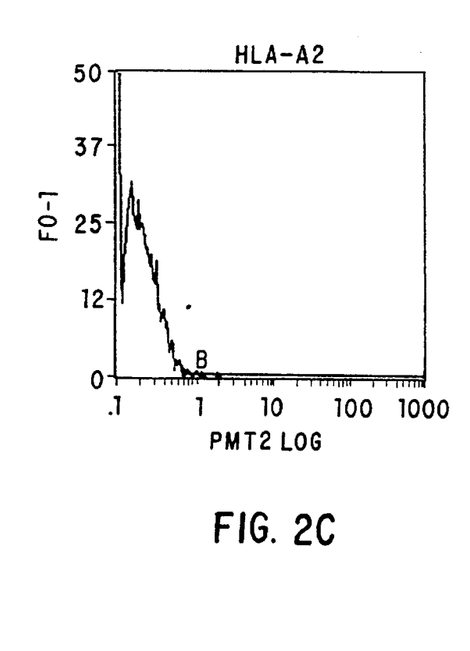
Figure 2D:
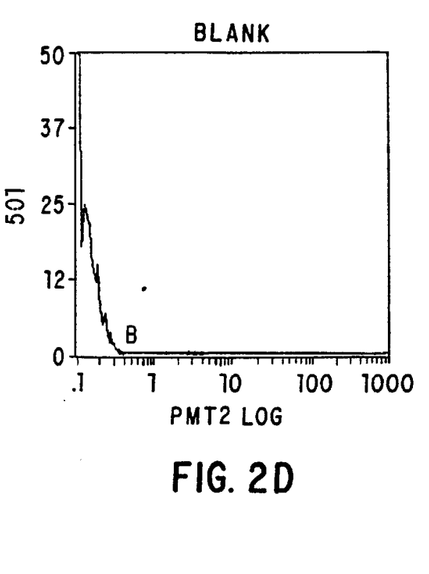
Figure 2E:
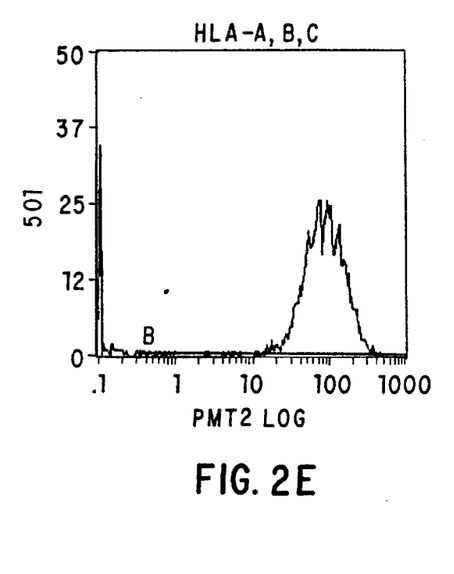
Figure 2F:
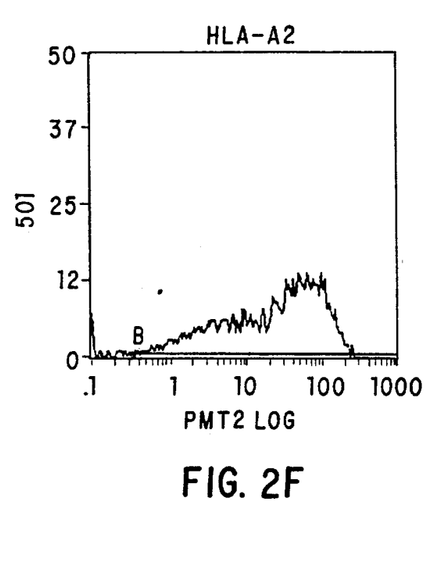
Figure 2G:
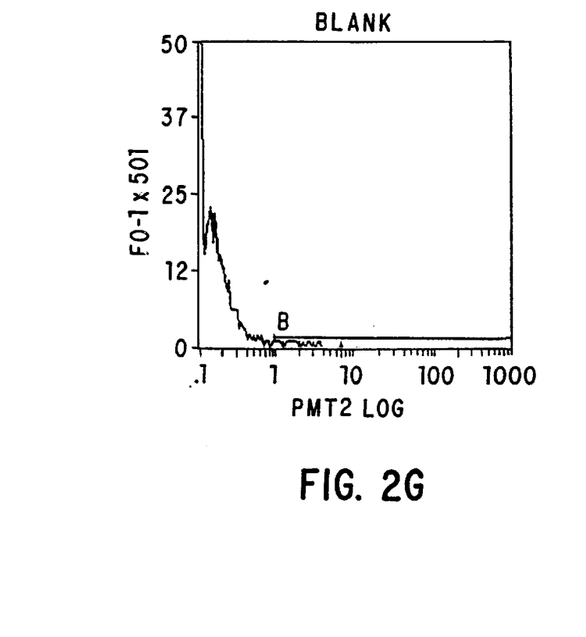
Figure 2H:
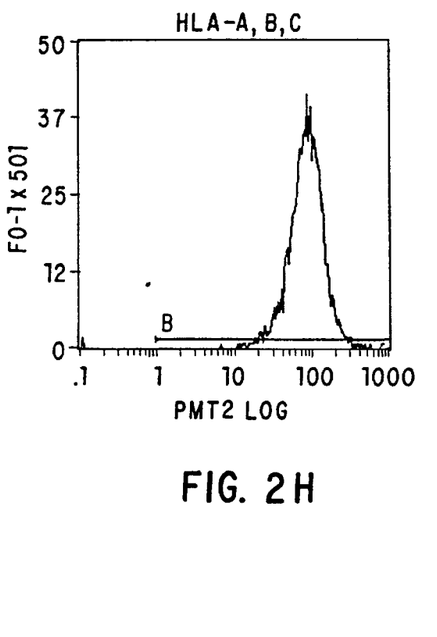
Figure 2I:
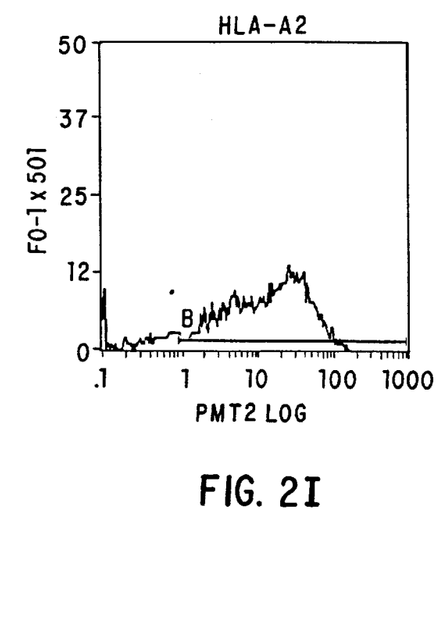

Subsequently, a cell survival curve for FO-1-neo transfectants exposed to γ-rays was generated. Specifically, single-cell suspensions in complete medium were irradiated with a single dose of γ-rays, ranging from 3 to 20 Gy, using a $^{137}$Cs γ-radiator (J. L. Shepherd and Assoc.) delivering 6 Gy/min. Irradiated cells were plated in cell culture dishes with complete medium, and surviving clones were scored two weeks after irradiation by their ability to form colonies, which were counted following fixation and staining with Giemsa (FIG. 1). The result of these cell survival experiments indicated that a single dose of 25 Gy would be sufficient to inactivate $\sim 1 \times 10^{12}$ cells. Therefore, this radiation dose was selected as a standard for inactivation of cells.

The coexistence in these engineered cells of a dominant marker (e.g., neomycin-resistance) and a recessive mutation (e.g., hgprt⁻) are necessary and sufficient for the easy selection of semiallogeneic cell hybrids (e.g., following PEG-mediated fusion of FO-1 transfectants with patient-derived tumor or white blood cells as described below) provided by the present invention.

Although only a single clone (FO-1 #12) was selected for use in the subsequent experimentation, given the teaching of the present specification, it is expected that other cells having the characteristics of the exemplary FO-1 #12 cells are within the scope of routine repetition of the above described steps.

Generation of Tumor Cell Hybrids

Polyethylene glycol(PEG)-mediated cell fusion (26) between neomycin-resistant, hgprt⁻ (HAT-sensitive) FO-1 #12 cells, and 501 human melanoma cells, was conducted according to the procedure by Prado et al (27). When fusing FO-1 #12 cells with cells in suspension (e.g., patient-derived white blood cells), the so-called stirring protocol is used (28).

Experiments of PEG-mediated cell fusion were carried out between FO-1 #12 and 501 human melanoma cells. Neomycin-resistant and HAT-resistant melanoma cell hybrids (FO-1 #12×501) were subjected to immunofluorescent staining using anti-HLA-A,B,C+$\beta_2$-microglobulin mAb W6-32 and anti-HLA-A2 mAb PA2.1, followed by affinity-isolated fluorescein-labeled goat anti-mouse immunoglobulin (FIG. 2).

The expression by FO-1 #12×501 cells of HLA-A2 surface antigen derived specifically from 501 parental cells confirmed that true hybrids had been obtained.

More recently, cell hybrids derived from the PEG-mediated fusion of FO-1 #12 cells with patient-derived tumor cells were generated and characterized. These patient-derived cells were obtained from tumor lesions removed as part of standard surgery and were in excess of the patients' needs. The resulting hybrids expressed HLA class I antigens.

So far, tumor cell hybrids from twenty-eight independent experiments of PEG-mediated cell fusion have been obtained, including: two human melanoma cell lines; one human prostatic carcinoma cell line; eleven patient-derived primary melanoma cell suspensions; two patient-derived primary colon carcinoma cell suspensions; eight patient-derived lung carcinoma cell suspension; two patient-derived breast carcinoma cell suspensions; and two white blood cell lines.

Survival curves of tumor cell hybrids following exposure to γ-radiation were generated and the results of these studies indicate that tumor cell hybrids are as radiation-sensitive as parental FO-1 #12 cells; therefore, 25 Gy γ-ray (at 6 Gy/min) was adopted as a standard lethal dose to inactivate hybrids for vaccine purposes.

Tumor cell hybrids tailored to and specific for each patient can be generated with cell suspensions from any solid tumor or from white blood cells; they can be propagated and irradiated for the purpose of therapeutic vaccination. Moreover, irradiated tumor cell hybrid vaccines can be formulated with appropriate cytokines (IL-12, GM-CSF, IL-2, etc.) for enhanced efficacy.

Derivation of White Blood Cells (Peripheral Mononuclear Lymphocytes) from Peripheral Blood Peripheral mononuclear lymphocytes (PML) are obtained from 20 ml of heparinized human blood. After diluting blood with Hank's balanced salt solution (HBSS) at a 1:1 ratio, the suspension is layered over the separation medium (Lymphocyte Separation Medium- LMS- Organon Teknika) and spun down at 400 xg at room temperature for 15–30 min. Centrifugation sediments erythrocytes and polynuclear leukocytes and bands mononuclear cells which can be aspirated, transferred to a centrifuge tube and diluted with an equal volume of HBSS. The mononuclear lymphocyte suspension is spun down for 10 min at room temperature at a speed sufficient to sediment the cells without damage (i.e., 160–260 xg). Cells are washed again in UBSS, resuspended in appropriate diluent and counted before using them for fusion.

Derivation of Tumor Cell Suspensions from Surgically Excised Lesions

The present protocol is a modification of the tumor disaggregation protocol by Berd et al (29). Tumors are retrieved immediately after excision from each patient, put in Hank's balanced salt solution (HBSS) on ice, and transported to the laboratory. Tumor specimens are then transferred under sterile conditions to a 100 mm culture dish containing HBSS. After separating fat and necrotic tissue away from tumor tissue (1–2 grams), the latter is minced into pieces as small as possible using scalpel blades.

Minced tumor tissue fragments are transferred to flasks containing 25–50 ml of an enzymatic solution made of Hank's balanced salt solution (HBSS), containing type I collagenase (3.5 mg/ml, Worthington) and deoxyribonuclease (Dnase) I (2.5 mg/ml, Sigma). The flask containing tumor cells is incubated at 37° C. for 30–60 minutes in a shaker incubator. The digested tumor cell suspension is then filtered through a sterile Nitex 40 nylon filter (mesh size 95 $\mu$m) to exclude undigested tumor fragments. This process is repeated once or twice more on undigested tissue fragments. Each cell suspension is transferred into a 50 ml conical centrifuge tube and spun at 250 xg for 5 min at 4° C. in a refrigerated centrifuge, washed once with HBSS, and resuspended in 5 ml of Red Blood Cell Lysis Buffer (Sigma) for 5–10 minutes to remove red blood cells. The resulting single cell suspension is counted and checked for viability by trypan blue exclusion test, before fusion with FO-1 #12 cells (see below). During processing, all solutions include gentamicin (50 $\mu$g/ml).

Formation, Propagation, and Irradiation of Tumor Cell Hybrids

The procedure outlined below is a variation of the one reported by Prado et al (27) for the PEG-mediated fusion of somatic cells in monolayers. Thus, a preferred choice for fusing agent is high quality PEG-1450 (purchased from ATCC) which has been pretested for cytotoxicity.

Single-cell suspensions of patient-derived tumor cells ($1 \times 10^7$ cells/100 mm dish) are plated on tissue culture dishes in DMEM supplemented with 10% FBS, streptomycin (100 μg/ml) and gentamicin (10 μg/ml). The following day, $4 \times 10^6$ FO-1 #12 cells are added to each dish of patient-derived cells for co-cultivation. After 4–5 hours of co-cultivation, cells are rinsed twice with serum-free DMEM prewarmed at 37°(D37°), and exposed for 5 min to 50 AM sodium dodecylsulfate (SDS) in D37°. SDS-containing medium is suctioned off and the monolayer is treated with 3 ml/dish of 50% PEG in D37°for fusion. The PEG solution is suctioned off and the monolayer rinsed three times with D37°before adding complete medium containing 15 μg/ml hypoxanthine, 0.2 μg/ml aminopterin, 5 μg/ml thymidine (HAT). The day following PEG-mediated cell fusion, selection for tumor cells hybrids is started in complete medium containing HAT and 600 μg/ml of the neomycin analog geneticin (G418). Cell hybrids derived from the fusion of FO-1 #12 cells with patient-derived cells are selected by virtue of their HAT-resistant and neomycin-resistant phenotype and are propagated in selective medium for several weeks.

When fusing FO-1 #12 cells with cells in suspension (e.g., patient-derived peripheral mononuclear lymphocytes (PML)), a modification of the stirring protocol is used (28). Patient-derived cells (PML) and FO-1 #12 cells are washed by centrifugation in D37°and then mixed at an approximate 5:1 ratio (25 million PML:5 million FO-1 #12 cells). The resulting cell mixture is then spun at 200 xg for 5 min in D37°containing 50 μM SDS. The mixed cell pellet is resuspended in 1 ml 50% PEG added slowly over 1 minute, and then stirred for an additional minute. Next, 10 mls D37° is slowly added over 2 minutes while stirring. The cell suspension is then centrifuged at 300 xg for 5 min. The cell pellet is resuspended in complete medium containing 15 μg/ml hypoxanthine, 0.2 μg/ml aminopterin, 5 μg/ml thymidine (HAT). The day following PEG-mediated cell fusion, selection for cell hybrids is started in complete medium containing HAT and 600 μg/ml of the neomycin analog geneticin (G418). Cell hybrids derived from the fusion of FO-1 #12 cells with patient-derived PML are selected by virtue of their HAT-resistant and neomycin-resistant phenotype and are propagated in selective medium for several weeks.

The HAT-resistant and neomycin-resistant cell population is subjected to immunofluorescent staining using anti-HLA class I antigen mAb W6-32, followed by affinity-isolated fluorescein-labeled goat anti-mouse immunoglobulin. The surface expression by HAT-resistant and neomycin-resistant cells of HLA class I antigens indicates that true hybrids have been obtained. As an additional confirmation, tissue typing of patient-derived white blood cells and semiallogeneic cell hybrids is performed in the HLA Tissue-Typing Laboratory.

Determination of Sterility and Endotoxin Activity

Immediately before freezing several aliquots of semiallogeneic cell hybrids, a sample of antibiotic-free cells are sent to an accredited laboratory for testing of sterility and endotoxin activity. These procedures are routine and have been published and practiced in this art.

Preparation of Irradiated Hybrids

After verification that the vaccine material is sterile and endotoxin-free, the hybrids are used to prepare the irradiated vaccine for injection. $5 \times 10^6$ cell hybrids (sufficient for 1 injection of vaccine at the minimum dose) are washed three times in HBSS, resuspended in 4 ml of HBSS, tested for viability by trypan blue exclusion (at least 70% viability is acceptable), and exposed to a single dose of about 25 Gy γ-rays at about 6 Gy/min, sufficient to kill all cell hybrids. Irradiated cell hybrids are spun down at 250 xg for 5 min and resuspended in 0.15 ml PBS before injection. To insure uncompromised vaccine efficacy, the time-lapse between irradiation and vaccine administration should not exceed about two hours. Cell hybrids are easily propagated and their numbers expanded to freeze down several aliquots of $\sim 5 \times 10^6$ (or more) cell hybrids for additional vaccinations.

Samples of cell hybrids from each patient can be identified by some accepted identifier (e.g., the patient's initials followed by their hospital registration number and the letters FO1.

Vaccine Formulation

The amount of irradiated hybrid administered will depend on the subject, the condition of the subject, the size of the subject, etc. The vaccine can be formulated with adjuvants and with additional compounds, including cytokines, in a pharmaceutically acceptable carrier.

The pharmaceutically acceptable carrier or adjuvant in the vaccine of the present invention can be selected by standard criteria (Arnon, R. (Ed.) Synthetic Vaccines I:83–92, CRC Press, Inc. Boca Raton, Fla., 1987). By "pharmaceutically acceptable" is meant a material that is not biologically or otherwise undesirable, i.e., the material may be administered to an individual along with the selected compound without causing any undesirable biological effects or interacting in a undesirable manner with any of the other components of the pharmaceutical composition in which it is contained. The carrier or adjuvant may depend on the method of administration and the particular patient.

Parenteral administration is generally characterized by injection. Injectables can be prepared in conventional forms, either as liquid solutions or suspensions, solid forms suitable for solution or suspension in liquid prior to injection, or as emulsions. A more recently revised approach for parenteral administration involves use of a slow release or sustained release system, such that a constant level of dosage is maintained. See, e.g., U.S. Pat. No. 3,710,795, which is incorporated by reference herein.

Other methods of administration can be by oral, sublingual, or any mucosal means, inhaled, absorbed. Actual methods of preparing the appropriate dosage forms are known, or will be apparent, to those skilled in this art; for example, see *Remington's Pharmaceutical Sciences* (Martin, E.W. (ed.) latest edition Mack Publishing Co., Easton, Pa.

Throughout this application various publications are referenced by numbers within parentheses. Full citations for these publications are as follows. The disclosures of these publications in their entireties are hereby incorporated by reference into this application in order to more fully describe the state of the art to which this invention pertains.

References

1. Boon, T. Toward a genetic analysis of tumor rejection antigens. Adv Cancer Res, 58:177–210, 1992.
2. Kawakami, Y, Eliyahu, S, Delgado, C H, Robbins, P F, Rivoltini, L, Topalian, S L, Miki, T, and Rosenberg, S A. Cloning of the gene coding for a shared human melanoma antigen recognized by autologous T cells infiltrating into tumor. Proc Natl Acad Sci USA, 91:3515–3519, 1994.

3. Kawakami, Y, Eliyahu, S, Delgado, C H, Robbins, P F, Sakaguchi, K, Appella, E, Yannelli, J R, Adema, G J, Miki, T, and Rosenberg, S A. Identification of a human melanoma antigen recognized by tumor-infiltrating lymphocytes associated with in vivo tumor rejection. Proc Natl Acad Sci USA, 91:6458–6462, 1994.

4. Brichard, V, Van Pel, A, Wolfel, T, Wolfel, C, De Plaen, E, Lethe, B, Coulie, P, and Boon, T. The tyrosinase gene codes for an antigen recognized by autologous cytolytic T lymphocytes on HLA-A2 melanomas. J Exp Med, 178:489–495, 1993.

5. Chen, L, Ashe, S, Brady, W A, Hellstrom, K E, Ledbetter, J A, McGowan, P, and Linsley, P S. Costimulation of antitumor immunity by the B7 counterreceptor for the T lymphocyte molecules CD28 and CTLA-4. Cell, 71:1093–1102, 1992.

6. Townsend, S E and Allison, J P. Tumor rejection after direct costimulation of CD8+T cells by B7-transfected melanoma cells. Science, 259:368–370, 1993.

7. Plautz, G E, Yang, Z Y, Wu, B Y, Gao, X, Huang, L, and Nabel, G J. Immunotherapy of malignancy by in vivo gene transfer into tumors. Proc Natl Acad Sci USA, 90:4645–4649, 1993.

8. Oettgen, H F and Old, L J. "The history of cancer immuno-therapy" in: Biologic Therapy of Cancer, DeVita, V T Jr, Hellman, S, and Rosenberg, S A, Eds., J. B. Lippincott Co., Philadelphia, 1991, pp. 87–119.

9. Gastl, G A, Abrams, J S, Nanus, D M, Osterkamp, R, Silver, J, Liu, F, Chen, M, Albina, A P, and Bander, N H. Interleukin-10 production by human carcinoma cell lines and its relationship to interleukin-6 expression. Int J Cancer, 55:96–101, 1993.

10. D'Andrea, A, Aste-Amezaga, M, Valiante, N M, Ma, X, Kubin, M, and Trinchieri, G. Interleukin-10 (IL-10) inhibits human lymphocyte interferon-gamma production by suppressing natural killer cell stimulatory factor/IL-12 synthesis in accessory cells. J Exp Med, 178:1041–1048, 1993.

11. Trip, C S, Wolf, D F, and Unanue, E R. Interleukin-12 and tumor necrosis factor alpha are costimulators of interferon gamma production by natural killer cells in severe combined immunodeficiency mice with listeriosis, and interleukin-10 is a physiologic antagonist. Proc Natl Acad Sci USA, 90:3725–3729, 1993.

12. Jami, J and Ritz, E. Expression of tumor-specific antigens in mouse somatic cell hybrids. Cancer Res, 33:2524–2528, 1973.

13. Parkman, R. Tumor cell hybrids: an immunotherapeutic agent. J Natl Cancer Inst, 52:1541–1545, 1974.

14. Kim, B S, Liang, W, and Cohen, E P. Tumor-specific immunity induced by somatic hybrids. I. Lack of relationship between immunogenicity and tumorigenicity of selected hybrids. J Immunol, 123:733–738, 1979.

15. Kim, BS. Tumor-specific immunity induced by somatic hybrids. II. Elicitation of enhanced immunity against the parent plasmocytoma. J Immunol, 123:739–744, 1979.

16. Payelle, B, Poupon, M-F, and Lespinats, G. Adoptive transfer of immunity induced by semi-allogeneic hybrid cells, against a murine fibrosarcoma. Int J Cancer, 27:783–788, 1981.

17. Toffaletti, D L, Darrow, T L, and Scott, D W. Augmentation of syngeneic tumor-specific immunity by semiallogeneic cell hybrids. J Immunol, 130:2982–2986, 1983.

18. Stott, E J. Anti-cell antibody in macaques. Nature, 353:393, 1991.

19. Almond, N, Kent, K, Chan, L, Page, M, Mills, K, Kitchin, P, Cranage, M, Li, J, Sodroski, J, Rud, E, and Stott, E J. Protection against SIV in macaques-implications for AIDS vaccine development. Biotech 94, Biotechnology Against AIDS Conference, Abstract 209, April 1994.

20. Chovaib, S, Chehimi, J, Bani, L, Genetet, N, Tursz, T, Gay, F, Trinchieri, G, and Mami-Chovaib, F. Interleukin 12 induces the differentiation of major histocompatibility complex class I-primed cytotoxic T-lymphocyte precursors into allogeneic cytotoxic effectors. Proc Natl Acad Sci USA 91:12659–12663, 1994.

21. Giovanella, B C, Stehlin, J S, Santamaria, C, Yim, S O, Morgan, A C, Williams, L J, Leibovitz, A, Fialkow, P J, and Mumford, D M. Human neoplastic and normal cells in tissue culture. I. Cell lines derived from malignant melanomas and normal melanocytes. J Natl Cancer Inst, 56:1131–1142, 1976.22.

22. D'Urso, C M, Wang, Z, Cao, Y, Tatake, R, Zeff, R A, and Ferrone, S. Lack of HLA class I antigen expression by cultured melanoma cells FO-1 due to a defect in $\beta_2$m gene expression. J Clin Invest, 87:284–292, 1991.

23. Kageshita, T, Wang, Z, Calorini, L, Yoshi, A, Kimura, T, Ono, T, Gattoni-Celli, S, and Ferrone, S. Selective loss of human leukocyte class I allospecificities and staining of melanoma cells by monoclonal antibodies recognizing monomorphic determinants of human leukocyte class I antigens. Cancer Res, 53:3349–3354, 1993.

24. Wigler, M, Pellicer, A, Silverstein, S, and Axel, R. Biochemical transfer of single copy eukaryotic genes using total cellular DNA as donor. Cell, 14:725–731, 1978.

25. Gorman, C, Padmanabhan, R. and Howard, B H. High efficiency DNA-mediated transformation of primate cells. Science, 221:551–553, 1983.

26. Pontecorvo, G. Production of mammalian somatic cell hybrids by means of polyethylene glycol treatment. Somatic Cell Genet. 1:397–400, 1975.

27. Prado, A A, Partearroyo, M A, Mencia, M, Goni, F M, and Barbera-Guillem, E. Surfactant enhancement of polyethyleneglycol-induced cell fusion. FEBS Lett, 259:149–152, 1989.

28. Galfre, G, Howe, S C, Milstein, C, Butcher, G W, and Howard, J C. Antibodies to major histocompatibility antigens produced by hybrid cell lines. Nature, 266:550–552, 1977.

29. Berd, D, Maguire, H C Jr, and Mastrangelo, M J. Induction of cell mediated immunity to autologous melanoma cells and regression of metastases after treatment with a melanoma cell vaccine preceded by cyclophosphamide. Cancer Res, 46:2572–2577, 1986.

What is claimed is:

1. A cell designated FO-1 #12, deposited with the American Type Culture Collection under accession Number ATTCC CRL-12177.

2. A cell hybrid formed by the fusion of the cell of claim 1 and a mammalian cell.

3. The cell hybrid of claim 2, wherein the hybrid is irradiated.

4. The cell hybrid of claim 2, wherein the mammalian cell is a patient-derived human cell.

5. The cell hybrid of claim 2, wherein the mammalian cell is a patient-derived tumor cell.

6. The cell hybrid of claim 5, in the patient-derived tumor cell is a melanoma cell.

7. The cell hybrid of claim 5, wherein the patient-derived tumor cell is a prostatic carcinoma cell.

8. The cell hybrid of claim 5, wherein the patient-derived tumor cell is a colon carcinoma cell.

9. The cell hybrid of claim 5, wherein the patient-derived tumor cell is a lung carcinoma cell.

10. The cell hybrid of claim 5, wherein the patient-derived tumor cell is a breast carcinoma cell.

11. The cell hybrid of claim 5, wherein the patient-derived tumor cell is a pancreatic carcinoma cell.

12. The cell hybrid of claim 4, wherein the patient-derived cell is a white blood cell.

13. A method of treating a solid tumor in a patient, comprising administering to the patient by intradermal injection the irradiated cell hybrid of claim 5, wherein the patient-derived tumor cell is derived from the patient being treated and wherein said administration results in a decrease in growth of said solid tumor.

14. The method of claim 13, wherein the cell hybrid is administered in conjunction with a cytokine.

15. The method of claim 13, wherein the cytokine is IL-2.

16. The method of claim 13, wherein the cytokine is granulocyte-macrophage colony-stimulating factor.

17. The method of claim wherein the cytokine is IL-12.

* * * * *

UNITED STATES PATENT AND TRADEMARK OFFICE
CERTIFICATE OF CORRECTION

PATENT NO. : 6,063,375 Page 1 of 1
DATED : May 16, 2000
INVENTOR(S) : Sabastiano Gattoni-Celli et al.

It is certified that error appears in the above-identified patent and that said Letters Patent is hereby corrected as shown below:

Column 10,
Line 53, please delete "ATTCC" and insert therefor -- ATCC --.
Line 62, after "5," please delete "in" and insert therefor -- wherein --.

Column 12,
Line 6, after "claim", please delete "13" and insert therefor -- 14 --.
Line 7, after "claim", please delete "13" and insert therefor -- 14 --.
Line 9, after "claim" and before "wherein", please insert -- 14, --.

Signed and Sealed this

Second Day of September, 2003

JAMES E. ROGAN
*Director of the United States Patent and Trademark Office*